(12) United States Patent
Bowen

(10) Patent No.: US 6,242,421 B1
(45) Date of Patent: Jun. 5, 2001

(54) METHODS FOR PREVENTING AND TREATING ALZHEIMER'S DISEASE

(76) Inventor: Richard Lloyd Bowen, 2500 N. Tamiami Trail, #116, Naples, FL (US) 34103

( * ) Notice: Subject to any disclaimer, the term of this patent is extended or adjusted under 35 U.S.C. 154(b) by 0 days.

(21) Appl. No.: 09/326,180

(22) Filed: Jun. 4, 1999

Related U.S. Application Data

(63) Continuation-in-part of application No. 09/040,906, filed on Mar. 18, 1998, now abandoned.
(60) Provisional application No. 60/063,982, filed on Nov. 6, 1997.

(51) Int. Cl.$^7$ ............. A61K 38/00; A61K 31/58
(52) U.S. Cl. ............................. 514/15; 514/176
(58) Field of Search ..................... 514/15, 176

(56) References Cited

U.S. PATENT DOCUMENTS

| | | | |
|---|---|---|---|
| 4,005,063 | 1/1977 | Gendrich et al. | 260/112.5 LH |
| 4,024,248 | 5/1977 | Konig et al. | 424/177 |
| 4,075,192 | 2/1978 | Nicolaides | 260/112.5 LH |
| 4,100,274 | 7/1978 | Dutta et al. | 424/177 |
| 4,234,571 | 11/1980 | Nestor et al. | 424/177 |
| 4,244,946 | 1/1981 | Rivier et al. | 424/177 |
| 4,762,717 | 8/1988 | Crowley, Jr. | 424/425 |

OTHER PUBLICATIONS

Yaffe et al., "Estrogen Therapy in Postmenopausal Women: Effects on Cognitive Function and Dementia," 279(9), 688 (Mar. 4, 1998), pp. 1, 7.

Roses, "Alzheimer's Disease and the Dementias," Sci. Am. Neuro XI 1 (Jun. 1997), p. 9.

Smalheiser et al., "Linking Estrogen to Alzheimer's Disease: An Informatics Approach" Neurology 47:809–810 (1996).

Amadeo, "Antiandrogen Treatment of Aggressivity in Men Suffering from Dementia," J. Geriat. Psychiat. & Neurol. 9(3):142 (Jul. 1996).

*Primary Examiner*—Theodore J. Criares
(74) *Attorney, Agent, or Firm*—Charles J. Prescott

(57) ABSTRACT

A method for treating Alzheimer's disease or preventing or delaying its onset in individuals deemed by competent observation and testing to be susceptible thereto. A non-estrogenic, non-androgenic, non-anabolic agent is dministered to reduce or eliminate blood serum levels of one or both of FSH and LH.

13 Claims, No Drawings

METHODS FOR PREVENTING AND TREATING ALZHEIMER'S DISEASE

This application is a continuation-in-part of application Ser. No. 09/040,906, filed Mar. 18, 1998, now abandoned, which claims the benefit of Provisional application 60/063,982 filed Nov. 6, 1997.

The present invention concerns methods for preventing or delaying the onset of Alzheimer's disease ("AD") in persons susceptible to the disease and for treating or slowing the development of the disease in persons suffering therefrom.

BACKGROUND OF THE INVENTION

"Alzheimer's disease" ("AD") is the term used to describe one of several "dementing disorders," brain diseases that progressively lead to loss of mental and physical functions, regardless of the age of onset. The cause(s) of AD remain(s) unknown. See, e.g., R. D. Teny, J. Neuropathol. Exper. Neurol. 55, 1023 (1996); D. J. Selkoe, Science 275,630 (1997).

AD is a major health-care problem. About 3 to 5 percent of older people suffer from the disease. A small fraction of Alzheimer's patients, i.e., persons suffering from AD, are under 50 years of age. Most are over 65. About 1 percent of the population aged 65–74 has the disease, increasing to about 5 percent of those aged 75–84 and to about 20 percent of those 85 or older. At least half the people in U.S. nursing homes have AD. The annual cost of caring for individuals with AD in institutional and community settings in the U.S. is about $40 billion for direct costs alone. As the population ages, the number of Alzheimer's patients and the costs of their care will rise as well.

In some cases, genetics plays a role in the risk of developing the disease. Thus, there are cases of familial Alzheimer's, in which related individuals are more likely to develop the disease because of common genetic factors. A genetic basis has been identified through the discovery of several genetic markers on chromosomes 1, 14 and 21 for a small subgroup of families in which the disease has frequently occurred at relatively early ages (beginning before age 50). Some evidence points to the gene on chromosome 19 for a protein, Apolipoprotein E ("Apo-E"), as implicated in certain other families that have frequently had the disease develop in family members at later ages; in these people, the gene encodes one particular variant, Apo-E4, of the several known variants of the Apo-E protein. Almost all persons who suffer from Down's Syndrome, which is caused by having three, rather than the normal two, copies of chromosome 21, develop Alzheimer's disease if they live to at least age 50. Alzheimer's disease is much more common among older women than older men. At age 80, the frequency of Alzheimer's disease among women is twice that among men. At age 90, the frequency among women is six times that among men.

Certain environmental factors are also thought to play a role in the development of the disease. High concentrations of aluminum may increase the risk of developing the disease. It is known that the incidence of the disease is lower among smokers than among non-smokers, leading to speculation that this is due to cholinergic activation by (−)–nicotine.

Alzheimer's disease can be diagnosed postmortem from microscopic abnormalities found in brain tissue. See "Consensus Recommendations for the Postmortem Diagnosis of Alzheimer's Disease," in Neurobiology of Aging (in the press), pre-published on the World-wide Web at the site for the Alzheimer Research Forum at http://www.alzforum.org/members/forums/consensus/index.html. The two principal abnormalities are senile or neuritic plaques (chemical deposits consisting of degenerating nerve cells combined with a form of protein called beta amyloid) and neurofibrillary tangles (malformations within nerve cells). The brains of AD patients of all ages reveal these abnormalities on autopsy examination. The plaques found in the brains of people with AD appear to be made, in part, from protein molecules—amyloid precursor protein ("APP")—that normally are essential components of the brain. Plaques are made when an enzyme snips APP apart at a specific place and then leaves the fragments—beta amyloid—in brain tissue where they come together in abnormal deposits. It has not as yet been definitely determined how neurofibrillary tangles are formed. Other abnormal anatomical and chemical changes associated with the disease have also been found. These include nerve-cell degeneration in the brain's nucleus basalis of Meynert and reduced levels of the neurotransmitter acetylcholine in the brain. But from a practical standpoint, the "classical" plaque and tangle changes seen in the brain at autopsy typically suffice for a diagnosis of AD. In fact, it is still only through the postmortem study of brain tissue from a person who was thought to have AD that a definitive diagnosis of the disorder can be made.

Brain scans, by one or more of computer-assisted tomography, positron-emission tomography, single photon emission computerized tomography, magnetic-resonance imaging and the like are known to be useful to discern changes characteristic of Alzheimer's disease in living patients as these changes become more evident with progression of the disease. These methods can also be useful in distinguishing from Alzheimer's disease certain other disorders that mimic Alzheimer's disease and might be reversible with appropriate treatment.

There are certain biochemical diagnostic "markers" that suggest that a person has or is developing AD and that can be detected without a brain biopsy while the person is living. Tests based on markers for the presence of or susceptibility to the disease are being developed. Among these markers are the occurrence in cerebrospinal fluid of elevated levels of the tau protein that occurs in lesions in the brains of persons with AD and the occurrence of mutations in the genes for two of the proteins that make up the cytochrome oxidase complex in mitochondria of persons with AD. Some of these markers can be detected even before behavioral manifestations of the disease become apparent in a person in whom AD is developing.

"Clinical" features of AD, which can be used, alone or together with brain scanning techniques or assays for biochemical markers, to diagnose possible or probable AD in patients antemortem, are threefold: (1) dementia—significant loss of intellectual abilities such as memory capacity, severe enough to interfere with social or occupational functioning; (2) insidious onset of symptoms—subtly progressive and irreversible course with documented deterioration over time; (3) exclusion of all other specific causes of dementia by history, physical examination, laboratory tests and psychometric and other studies.

Based on these three criteria, the clinical diagnosis of AD has been referred to as "a diagnosis by exclusion," and one that can only be made in the face of clinical deterioration over time. There is no specific clinical test or finding that is unique to AD. Hence, a diagnosis of AD is made by systematically excluding or "ruling out" all other disorders that can bring on symptoms similar to those of Alzheimer's.

Because of the many other disorders that can be confused with AD, a comprehensive clinical evaluation offers the best chance of arriving at a correct diagnosis of symptoms that might indicate AD. Such an evaluation includes at least three major components: (1) a thorough general medical workup, which should include a detailed medical history, blood work, urinalysis, chest x-ray, electroencephalogram, computerized tomography scan, and electrocardiogram; (2) a neurological examination; and (3) a psychiatric evaluation that may include psychological or psychometric testing. See also, Diagnostic and Statistical Manual of Mental Disorders, 4$^{th}$ Edition, American Psychiatric Association, Washington D.C., U.S.A. (1994).

It is estimated that about 10% of persons diagnosed as having AD in fact do not have that disease but rather have another disease which has similar symptoms. Tragically, some of these other diseases may be treatable if diagnosed. But first they must be identified and not dismissed as AD or "senility."

Conditions that affect the brain and result in intellectual, behavioral, and psychological dysfimction are referred to as "organic mental disorders." These disorders represent a broad grouping of diseases and include AD. Organic mental disorders that can cause clinical problems like those of AD, and which might be reversible or controlled with proper diagnosis and treatment, include the following:

Side Effects of Medications: Unusual reactions to medications, too much or too little of prescribed medications, combinations of medications which, when taken together, cause adverse side effects.

Substance Abuse: Abuse of legal and/or illegal drugs, alcohol abuse.

Metabolic Disorders: Thyroid problems, nutritional deficiencies, anemias, etc.

Circulatory Disorders: Heart problems, strokes, etc.

Neurological Disorders: Normal-pressure hydrocephalus, multiple sclerosis, etc.

Infections: Especially viral or fungal infections of the brain.

Trauma: Injuries to the head.

Toxic Factors: Carbon monoxide, methyl alcohol, etc.

Tumors: Any type within the skull—whether originating or metastasizing there.

In addition to organic mental disorders resulting from these diverse causes, other forms of mental dysfunction or mental health problems can also be confused with AD. For example, severe forms of depression can cause problems with memory and concentration that initially may be indistinguishable from early symptoms of AD. Sometimes these conditions, referred to as "pseudodementia," can be reversed. Other psychiatric problems can similarly masquerade as AD and, like depression, respond to treatment.

In many cases, if a treatment or preventative for Alzheimer's would be available, a person diagnosed as likely having Alzheimer's but possibly having another disease or disorder with similar characteristics could be treated for both to be sure that the person is treated effectively.

Heretofore, only a limited number of pharmacological agents have been identified as effective in treating symptoms of AD in a person suffering therefrom. The most prominent of these today are tacrine and donepezil hydrochloride, which are cholinesterase inhibitors active in the brain. These drugs do not slow the progress of the disease. Other such cholinesterase inhibitors are being investigated for treating symptoms of the disease, as are certain cholinergic channel modulators (compounds which modulate functions of brain acetylcholine receptors).

No compound has been established as effective in blocking the development or progression of AD, although a number of compounds are thought to possibly have this capability and are being investigated for therapeutic use for this purpose. These compounds include the hormone estrogen, the non-steroidal anti-inflammatory ibuprofen, the anti-Parkinson's disease monoamine-B oxidase inhibitor selegiline (L-deprenyl), vitamin E, the compound propentofylline that stimulates release of nerve growth factor and inhibits reuptake of adenosine as a neurotransmitter, and the compound sabeluzole which is an antagonist of glutamate as a neurotransmitter and apparently is neuroprotective on account of stabilization of the neuronal cell cytoskeleton.

The present invention relates to levels in humans (as measured, for example, in serum) of the pituitary gonadotropins ("Gn's") follicle-stimulating hormone ("FSH") and luteinizing hormone ("LH"). It is known that these hormones are produced in response to gonadotropin releasing hormone ("GnRH"), which is also known as luteinizing hormone releasing hormone ("LHRH"). In the absence of GnRH, LH and FSH will not be made. Through a complex mechanism, sustained presence of high levels of GnRH will result in reduction in the levels of LH and FSH to the point that they have no detectable physiological activity (which means, for purposes of this application, that their levels are not detectable). Similarly, sustained presence of inhibin will result in reduction in the level of FSH to the point that it has no detectable physiological activity.

Not only GnRH but also the many known, physiologically active analogs thereof, some of which are agonists of GnRH, result in reduced levels of the gonadotropins, even to the point of indetectability, when they are maintained at physiologically active levels over sufficiently long periods of time. Similarly, inhibin and the many known physiologically active analogs thereof, some of which are agonists and others of which are antagonists of inhibin, result in reduced levels of FSH, even to the point of indetectability, when they are maintained at physiologically active levels over sufficiently long periods of time.

Reference herein to "GnRH analogs" means both GnRH and physiologically active analogs thereof. Reference herein to "inhibin analogs" means both inhibin and physiologically active analogs thereof.

It is also known that administration to a human of vaccines that cause production of antibodies that react with GnRH and inhibit its activity results in reduction, potentially to the point of indetectability, of FSH and LH.

Still further, administration to a human of vaccine-stimulated antibodies that react with FSH and LH inhibit the hormone's physiological activity, potentially to the point of indetectability.

Heretofore, no association has been recognized between AD and the level of LH or FSH. More specifically, it has not been recognized that reducing levels of Gn's will inhibit or prevent the development or progression of AD.

SUMMARY OF THE INVENTION

According to this invention, reducing the level of FSH or LH or both inhibits the progression of AD in a person suffering therefrom, and consequently can be used to treat the disease.

Further, according to this invention, reducing the level of FSH or LH or both inhibits the development of AD in a person susceptible to the disease. Thus, in accordance with this discovery, AD can be prevented in an individual by maintaining FSH, LH or both at levels that are sufficiently low (preferably indetectable) to be effective for such prevention.

Thus, the invention entails a method of treating AD in a person suffering therefrom and a method of preventing AD in a person susceptible thereto by administration to the person of an AD-treatment-effective amount or an AD-prevention-effective amount, respectively, of a compound or combinations which will reduce the level in the person (e.g., the level in the person's serum) of a hormone selected from the group consisting of FSH and LH. Among such compounds are those selected from the group consisting of GnRH analogs and physiologically acceptable salts thereof, inhibin analogs and physiologically acceptable salts thereof, vaccines that stimulate production of anti-GnRH antibodies, anti-inhibin antibodies, anti-FSH antibodies and anti-LH antibodies, or conjunctive administrations of such compounds.

DETAILED DESCRIPTION OF THE INVENTION

As indicated above, the invention entails treating AD in persons suffering therefrom and preventing AD in persons susceptible thereto.

A person "suffering from AD" is a person who has been diagnosed as having AD, by a practitioner of at least ordinary skill in the art of clinically diagnosing (e.g., diagnosing in patients antemortem) AD, using methods and routines, such as those described above, that are standard in the art of such clinical diagnoses.

By "treating AD" is meant slowing or preventing the progression or worsening of the disease that is now known to occur when the disease is untreated.

A person "susceptible" to AD is a person who has not been diagnosed, by a practitioner of at least ordinary skill in clinical diagnosis of AD, as suffering from the disease but for whom the probability of acquiring the disease, such that the person would be diagnosed as suffering from it, is significantly higher than for the general population. Thus, persons who are susceptible to AD include, for example, all persons who have not been diagnosed as definitely suffering from the disease but are suffering from Down's Syndrome due to trisomy 21, have been diagnosed by a practitioner of at least ordinary skill in clinical diagnosis of AD as possibly or probably but not definitely suffering from AD, have a genetic marker for familial AD, such as one of those that are now known on chromosomes 1, 14, 19 and 21, or who are 80 years old or older.

By "preventing" AD in a person susceptible thereto is meant preventing the development of the disease in such a person to the point that the person would be clinically diagnosed, by a practitioner of at least ordinary skill in the art of diagnosing AD, as definitely suffering from AD.

By "non-estrogenic, non-androgenic or non-anabolic steroidal" agents is meant agents that are not, respectively, estrogens or estrogen-like, androgens or androgen-like, or anabolic steroids or anabolic steroid-like.

In accordance with the invention, AD in a person suffering therefrom can be treated by administration to the person of any composition that reduces the person's level of a hormone selected from the group consisting of FSH and LH, in an amount and for a duration effective to bring about such a reduction.

Further, in accordance with the invention, AD can be prevented, or onset of clinical or behavioral manifestations delayed, in a person susceptible to the disease by administration to the person of any composition that reduces the level of a hormone selected from the group consisting of FSH and LH, in an amount and for a duration effective to bring about such a reduction to a level below which development of the disease will not occur.

Reference herein to "level of a hormone" in a person means concentration of the biologically active hormone in the person's serum. Typically, the level of a hormone will be reduced by reducing the concentration of the hormone itself. However, reducing the activity of the hormone—as, for example, by binding it with an antibody that blocks the hormone's activity—even if the concentration of the hormone remains the same, is considered reducing the level of the hormone for purposes of the present application. The serum concentrations of biologically active FSH and LH in a human can be determined by any of a number of methods well known to the skilled.

As understood in the art, vaccines that stimulate production of antibodies can be employed to bind to FSH, LH, or GnRH and block or at least substantially reduce their biological activities. Thus, vaccine-stimulated antibodies to FSH, LH or both can be employed in accordance with the invention to directly reduce the level of these hormones and thereby treat or prevent AD. Such antibodies to GnRH, by blocking its activity, will result in reduced levels of FSH and LH. These antibodies can be employed in accordance with the invention to reduce levels of FSH and LH, or FSH or LH alone, and thereby to prevent or treat AD.

Antibodies for use in accordance with the invention may be made by conventional methods for preparation of vaccine antibodies for therapeutic use in humans. The vaccine-stimulated antibodies may be polyclonal and from any antibody-producing species, such as mice, rats, horses, dogs or humans. The antibodies may also be, and preferably are, monoclonal from cultures of antibody-producing cells from an antibody-producing species such as mice, rats, horses, dogs, and humans. The term "antibody" as used herein, unless otherwise limited, also encompasses antigen-binding fragments, such as $F_{ab}$ fragments, of intact antibodies. If an antibody is monoclonal but from cultured cells of a species other than human, the antibody may be "humanized" by conventional methods to make it more tolerable immunologically to a person treated therewith. Antibodies for use in accordance with the invention can also be made by conventional techniques using cultured cells, preferably human cells, that have been genetically engineered to make a desired intact antibody or antigen-binding antibody fragment.

Antibodies will be administered in accordance with the invention by any method known in the art for administering same but preferably by intravenous injection of a sterile aqueous solution of the antibody, together with standard buffers, preservatives, excipients and the like.

Also useful in carrying out the invention are compounds that antagonize the activity of GnRH or stimulate production of inhibin in the production of FSH and LH. Thus, compounds that block the receptors for GnRH or stimulate receptors of inhibin on the pituitary, or that otherwise act on the pituitary-ovarian or pituitary-testicular axis to inhibit production or activity of GnRH or stimulate production of or activate inhibin, or to directly inhibit production of FSH or LH or both, will result in reduced levels of FSH and LH and can be employed in accordance with the invention to treat or prevent AD. One such compound is danazol (see The Merck Index, Merck & Co., Inc., Whitehouse Station, N.J., U.S.A 12th Ed. 1996 (hereinafter "Merck Index"), entry no. 2875, and U.S. Pat. No. 3,135,743). Such compounds, also, will be administered by any standard route as understood in the art.

As indicated above, GnRH analogs (or physiologically acceptable salts thereof) and inhibin analogs (or physiologically acceptable salts thereof) can also be used in accordance with the invention to treat or prevent AD by reducing levels of FSH and LH, or FSH or LH itself.

Preferred for use in the invention are GnRH analogs and pharmaceutically acceptable salts thereof that can be employed to reduce levels of FSH and LH to levels that are undetectable. Most preferred among these is leuprolide or goserelin, and especially leuprolide acetate and goserelin acetate.

GnRH analogs or salts thereof that may be employed in accordance with the invention include, among others, GnRH itself and its monoacetate and diacetate salt hydrates (Merck Index entry no. 5500) and the many analogs thereof that are known in the art. These include, for example, leuprolide and its monoacetate salt (Merck Index entry no. 5484, U.S. Pat. No. 4,005,063); the analogs of leuprolide with the D-leucyl residue replaced with D-α-aminobutyryl, D-isoleucyl, D-valyl or D-alanyl and the monoacetate salts thereof (U.S. Pat. No. 4,005,063); buserelin and its monoacetate salt (Merck Index entry no. 1527, U.S. Pat. No. 4,024,248); nafarelin and its monoacetate and acetate hydrate salts (Merck Index entry no. 6437, U.S. Pat. No. 4,234,571); deslorelin (Merck Index entry no. 2968); histrelin and its acetate salt (Merck Index entry no. 4760, U.S. Pat. No. 4,244,946); and goserelin and its acetate salt (Merck Index entry no. 4547, U.S. Pat. No. 4,100,274). For other GnRH analogs and salts thereof that can be used in accordance with the invention, see also U.S. Pat. No. 4,075,192, U.S. Pat. No. 4,762,717, and the U.S. patents cited at column 3, lines 49–54, of U.S. Pat. No. 4,762,717.

All of the U.S. patents cited herein, including those not cited specifically but cited at column 3, lines 49–54, of U.S. Pat. No. 4,762,717, and all of the Merck Index entries cited herein are incorporated herein by reference.

Administration of GnRH analogs, and inhibin analogs, in accordance with the invention will be by any method known in the art for administering same. Thus, administration may be by injection subcutaneously, intramuscularly or intravenously of a sterile aqueous solution which includes the analog together with buffers (e.g., sodium acetate, phosphate), preservatives (e.g., benzyl alcohol), salts (e.g., sodium chloride) and possibly various excipients or carriers. In this connection, see, for example, Physician's Desk Reference, 51$^{st}$ Ed., Medical Economics Co., Montvale, N.J., U.S.A. (1997), pp. 2736–2746 (leuprolide acetate) and pp. 2976–2980 (goserelin acetate), which are also incorporated herein by reference.

The dose and dosage regimen for a particular composition used to carry out the invention with a particular patient will vary depending on the active (i.e., LH-lowering or FSH-lowering) ingredient and its concentration and other components in the composition, the route of administration, the gender, age, weight, and general medical condition of the patient, and whether the patient is already suffering from AD. The skilled medical practitioner will be able to appropriately prescribe dosage regimens to carry out the invention. It is preferred in carrying out the invention that the concentrations of FSH or LH, preferably both, in a patient be reduced to and maintained at levels that are as low as possible. It is usually preferred that the concentrations of FSH and LH be reduced to indetectable levels. However, beneficial effects of preventing or reducing susceptibility to AD, or treating AD, are achieved even if the concentrations of FSH and LH are reduced but not to indetectable levels. Thus, the medical practitioner will select the composition, dose and dosage regimen for a particular patient to achieve and maintain such low concentrations of FSH, LH or both in the patient.

In carrying out the invention, compounds that block the receptors for GnRH or stimulate receptors of inhibin on the pituitary, or that otherwise act on the pituitary-ovarian or pituitary-testicular axis to inhibit production or activity of GnRH or stimulate production of or activate inhibin, or to directly inhibit production of FSH or LH or both, are administered at between about 0.1 g and 10 g per day.

In a most preferred embodiment of carrying out the invention, a composition comprising a GNRH analog will be administered intramuscularly or subcutaneously as a depot composition from which release of the analog into the patient's system will be sustained over a long period, from about a week to about six months or more. This will maintain the concentration of FSH or LH or both in the patient at the low or undetectable level(s) as described above without the pain, cost and inconvenience of much more frequent (e.g., daily) administration. Such depot compositions of GnRH analogs are known and their preparation is well within the skill of the ordinarily person skilled in the art. See, e.g., Physician's Desk Reference, 51$^{st}$ Ed. pp. 2736–2746 and 2976–2980, cited above.

To allow the skilled medical practitioner to easily establish doses and dosage regimens of GnRH analogs for treating or preventing AD in individual patients in accordance with the invention, doses and dosage regimens for goserelin acetate and leuprolide acetate are provided here. Doses of goserelin acetate effective to treat or prevent AD range from about 1 mg to about 10 mg, preferably about 4 mg, with a once monthly subcutaneous injection of a sterile depot formulation of from about 3 mg to about 30 mg, preferably about 10 mg, with a subcutaneous injection once every three months of a sterile depot formulation.

Doses of leuprolide acetate effective to treat or prevent AD range between about 0.2 and 20 mg/day, preferably about 1 mg/day, when the dosage regimen is by once daily, subcutaneous injection of sterile solution comprising the compound; between about 1 mg and about 10 mg, preferably about 5 mg, with a once monthly intramuscular injection of a sterile depot formulation comprising the compound; and between about 10 mg and about 50 mg, preferably about 25 mg, with an intramuscular injection once every three months of a depot formulation comprising the compound.

Information from data already available or easily obtained by routine experimentation on GnRH analogs in suppressing LH and FSH activity, those of ordinary skill can easily determine the dose and dosage regimens for any GnRH analog.

It must be noted that there would be no reason to use the methods of the invention for the purpose of treating or preventing AD in a person who suffers from a condition whereby the person either does not produce GnRH (and so does not produce LH or FSH). The levels of LH and FSH cannot be reduced in such a person by administering compounds in accordance with the method of the invention; and, as the skilled will understand, in the case of administering GnRH analogs to such a person, the levels of LH and FSH in the person might increase under certain circumstances.

For persons who do produce GnRH, and FSH or LH or both, treatment in accordance with the invention must be continuous for the duration of their lives. The reason for this need for continuous administration is that, once such administration is discontinued, the persons' natural production of GnRH, FSH and LH will resume within at most a few months or, more typically, within a few weeks.

The foregoing description, discussion and scope of the invention are directed to those of ordinary skill in the treatment of actual or incipient AD. Accordingly, it is to be expected that the teachings herein will enable selection of specific agents and regimens for treatment within the scope of the appended claims.

What is claimed is:

1. A method for treating or preventing Alzheimer's disease in a human subject in need thereof and producing FSH, LH or both comprising:

administering to said subject a therapeutically effective amount of at least one physiologically acceptable agent that reduces or eliminates blood serum levels of one or both of FSH and LH;

said agent being (1) GnRH, inhibin or analogs thereof, (2) anti-GnRH or anti-inhibin antibodies or (3) anti-FSH or anti-LH antibodies.

2. The method of claim 1 in which said agent is formulated as a sustained-release composition for intramuscular or subcutaneous injection.

3. A method for treating or preventing Alzheimer's disease in a human subject in need thereof and producing FSH, LH or both comprising:

administering to said subject a therapeutically effective amount of at least one physiologically acceptable agent that reduces or eliminates blood serum levels of one or both of FSH and LH;

said agent being GnRH, inhibin or analogs thereof.

4. A method for treating or preventing Alzheimer's disease in a human subject in need thereof and producing FSH, LH or both comprising:

administering to said subject a therapeutically effective amount of at least one physiologically acceptable agent that reduces or eliminates blood serum levels of one or both of FSH and LH;

said agent being anti-GnRH or anti-inhibin antibodies.

5. A method for treating or preventing Alzheimer's disease in a human subject in need thereof and producing FSH, LH or both comprising:

administering to said subject a therapeutically effective amount of at least one physiologically acceptable agent that reduces or eliminates blood serum levels of one or both of FSH and LH;

said agent being anti-FSH or anti-LH antibodies.

6. A method for treating or preventing Alzheimer's disease in a human subject in need thereof and producing FSH, LH or both comprising:

administering to said subject a therapeutically effective amount of at least one physiologically acceptable agent that reduces or eliminates blood serum levels of one or both of FSH and LH;

said agent being GnRH or analogs thereof.

7. The method of claim 6 in which said agent is leuprolide or physiologically acceptable analogs and salts thereof.

8. The method of claim 6 in which said agent is buserelin or physiologically acceptable analogs and salts thereof.

9. The method of claim 6 in which said agent is nafarelin or physiologically acceptable analogs and salts thereof.

10. The method of claim 6 in which said agent is deslorelin or physiologically acceptable analogs and salts thereof.

11. The method of claim 6 in which said agent is histrelin or physiologically acceptable analogs and salts thereof.

12. The method of claim 6 in which said agent is goserelin or physiologically acceptable analogs and salts thereof.

13. A method for treating Alzheimer's Disease in a human subject or preventing or delaying the onset of Alzheimer's Disease in a human subject deemed susceptible thereto and in need thereof, comprising:

administering to said subject a therapeutically effective amount of at least one physiologically acceptable non-estrogenic agent that reduces or eliminates blood serum levels of one or both of FSH and LH.

* * * * *